US009810629B2

(12) United States Patent
Li et al.

(10) Patent No.: US 9,810,629 B2
(45) Date of Patent: Nov. 7, 2017

(54) RECOGNITION OF POSITION OF CRYSTAL IN NUCLEAR DETECTOR

(71) Applicant: Shenyang Neusoft Medical Systems Co., Ltd., Shenyang (CN)

(72) Inventors: Nan Li, Shenyang (CN); Guodong Liang, Shenyang (CN); Yuqiu Zhao, Shenyang (CN); Guocheng Wu, Shenyang (CN); Jian Zhao, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 0 days.

(21) Appl. No.: 15/277,304

(22) Filed: Sep. 27, 2016

(65) Prior Publication Data

US 2017/0089833 A1 Mar. 30, 2017

(30) Foreign Application Priority Data

Sep. 30, 2015 (CN) .......................... 2015 1 0642229

(51) Int. Cl.
*G01N 21/63* (2006.01)
*G01T 7/00* (2006.01)

(52) U.S. Cl.
CPC .............. *G01N 21/63* (2013.01); *G01T 7/00* (2013.01)

(58) Field of Classification Search
CPC ............. G01T 7/00–7/125; G01T 1/16; G01T 1/1644; G01T 1/20–1/28; G01T 1/2985; G01N 21/62–21/658; A61B 6/037
See application file for complete search history.

(56) References Cited

U.S. PATENT DOCUMENTS 7,291,841 B2 * 11/2007 Nelson .................... G01T 1/243
 250/370.01
9,006,664 B2 * 4/2015 Zhang ................... G01T 1/2018
 250/363.01
(Continued)

FOREIGN PATENT DOCUMENTS

CA 2283771 A1 3/2000
CN 88100848 A 9/1988
(Continued)

OTHER PUBLICATIONS

Long An-Wen, et al; Energy calibration based on PET singles list mode date; Progress Report on China Nuclear Science & Technology (vol. 2), Oct. 2011; p. 138-142.
(Continued)

*Primary Examiner* — Huy Q Phan
*Assistant Examiner* — David Frederiksen
(74) *Attorney, Agent, or Firm* — Fish & Richardson P.C.

(57) ABSTRACT

An apparatus for recognizing a position of a crystal in a nuclear detector, including: a silicon semiconductor detector array arranged in a crystal array in the nuclear detector, where each row/or column of silicon semiconductor detectors is configured to output a sum of voltages outputted by the silicon semiconductor detectors in the row/or column at a row/or column signal output end; row signal comparing modules, one to one correspondingly connected to each row signal output end and configured to obtain a row comparison result for each row of silicon semiconductor detectors; column signal comparing modules, one to one correspondingly connected to each column signal output end and configured to obtain a column comparison result for each column of silicon semiconductor detectors; and a crystal position recognizing module configured to recognize a posi-
(Continued)

tion of a crystal hit by a photon according to each row comparison result and each column comparison result.

20 Claims, 8 Drawing Sheets

(56) References Cited

U.S. PATENT DOCUMENTS

| | | | |
|---|---|---|---|
| 2004/0124360 A1 | 7/2004 | Levin | |
| 2005/0006589 A1* | 1/2005 | Joung | G01T 1/202 250/370.09 |
| 2008/0205119 A1 | 8/2008 | Nagai et al. | |
| 2010/0044571 A1* | 2/2010 | Miyaoka | G01T 1/20 250/362 |
| 2010/0084559 A1 | 4/2010 | Aykac et al. | |
| 2011/0150181 A1* | 6/2011 | Cook | G01T 1/1648 378/86 |
| 2013/0009066 A1* | 1/2013 | Grazioso | G01T 1/1642 250/363.03 |
| 2014/0021354 A1* | 1/2014 | Gagnon | G01T 1/1647 250/362 |

FOREIGN PATENT DOCUMENTS

| | | |
|---|---|---|
| CN | 1190467 A | 8/1998 |
| CN | 101644780 A | 2/2010 |
| CN | 101833106 A | 9/2010 |
| CN | 102426503 A | 4/2012 |
| CN | 103797330 A | 5/2014 |
| CN | 104570042 A | 4/2015 |
| CN | 104597474 A | 5/2015 |
| JP | S63200088 A | 8/1988 |
| JP | H04303787 A | 10/1992 |
| JP | 2003-98262 A | 4/2003 |
| JP | 2014115094 A | 6/2014 |
| WO | 2008142590 A2 | 11/2008 |

OTHER PUBLICATIONS

State Intellectual Property Office of the People's Republic of China; Office action dated Aug. 8, 2017 in corresponding Chinese Patent Application No. 201510642229.X (with English-language translation).

* cited by examiner

RECOGNITION OF POSITION OF CRYSTAL IN NUCLEAR DETECTOR

CROSS REFERENCE TO RELATED APPLICATIONS

This application claims priority under 35 U.S.C. §119 to Chinese Patent Application No. 201510642229.X, filed on Sep. 30, 2015. The content of the priority application is hereby incorporated by reference in its entirety.

TECHNICAL FIELD

The present disclosure relates to recognition of a position of a crystal in a nuclear detector.

BACKGROUND

Nuclear medical devices, such as a Single-Photon Emission Computed Tomography (SPECT) device, a Positron Emission Tomography (PET) device and so on, may form an image based on distribution of drugs containing radionuclides in a human body, thereby reflecting human body metabolism, tissue functions and structural forms.

In nuclear medical devices, a nuclear detector may detect rays (for example, γ rays) emitted from radionuclides introduced into human bodies to be examined. A commonly-used nuclear detector may include a crystal array comprising a plurality of crystals and a photoelectric detector. The crystal array may be used for detecting photons (for example γ photons) released from a subject and converting the photons into visible light. The photoelectric detector may be used for converting the visible light into an electric signal. The electric signal may be used for calculating a position of a crystal hit by a photon of a ray to form a position scatter diagram, thereby forming an image of tissues of an irradiated subject.

In an example, a frequently-used photoelectric detector may include a photomultiplier tube (PMT). In order to completely convert visible light converted by a crystal into an electric signal, theoretically, a quantity ratio of crystals to PMTs should be 1:1. In order to improve a spatial resolution of a nuclear detector, a size of a crystal becomes smaller and smaller. However, since a size of a PMT is limited, in practical applications, the quantity ratio of PMTs to crystals generally is 1:n (n>1). Generally a PMT is round in shape and thus is unable to receive all visible light from a crystal. Due to this reason, a difference may likely exist between energy denoted by an electric signal outputted by the PMT and energy of visible light generated by the crystal, thereby causing an energy error.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

One aspect of the present disclosure features an apparatus for recognizing a position of a crystal in a nuclear detector, including: a silicon semiconductor detector array, comprising a plurality of silicon semiconductor detectors arranged in a form of a crystal array in the nuclear detector, wherein: each row of the silicon semiconductor detector array is configured to output a sum of voltages outputted by the silicon semiconductor detectors in the row at a row signal output end, each column of the silicon semiconductor detector array is configured to output a sum of voltages outputted by the silicon semiconductor detectors in the column at a column signal output end, each of the silicon semiconductor detectors corresponds to a crystal in the crystal array and is coupled to a row signal output end of a row including the silicon semiconductor detector and to a column signal output end of a column including the silicon semiconductor detector; a plurality of row signal comparing modules each coupled to a respective row signal output end of a respective row of the silicon semiconductor detectors and configured to obtain a row comparison result corresponding to the respective row of the silicon semiconductor detectors by comparing a voltage on the respective row signal output end with a threshold voltage; a plurality of column signal comparing modules each coupled to a respective column signal output end of a respective column of the silicon semiconductor detector and configured to obtain a column comparison result corresponding to the respective column of the silicon semiconductor detectors by comparing a voltage on the respective column signal output end with the threshold voltage; and a crystal position recognizing module coupled to each of the row signal comparing modules and each of the column signal comparing modules and configured to recognize a position of a crystal hit by a photon according to row comparison results outputted by the row signal comparing modules and column comparison results outputted by the column signal comparing modules.

In some implementations, the row signal comparing module includes a comparator configured to: output a high level as a row comparison result when a voltage on the row signal output end corresponding to the row signal comparing module is no less than the threshold voltage; and output a low level or a zero level as a row comparison result when a voltage on the row signal output end corresponding to the row signal comparing module is less than the threshold voltage.

In some implementations, the column signal comparing module includes a comparator configured to: output a high level as a column comparison result when a voltage on the column signal output end corresponding to the column signal comparing module is no less than the threshold voltage; and output a low level or a zero level as a column comparison result when a voltage on the column signal output end corresponding to the column signal comparing module is less than the threshold voltage.

The crystal position recognizing module can be configured to: read a row comparison result outputted by each of the row signal comparing modules and a column comparison result outputted by each of the column signal comparing modules, and recognize an intersection position of a row of silicon semiconductor detectors corresponding to a row comparison result with a high level and a column of silicon semiconductor detectors corresponding to a column comparison result with a high level, as the position of the crystal hit by a photon.

In some implementations, the apparatus further includes a plurality of samplers, respectively coupled to each of the row signal output ends and configured to obtain a sampled electric signal corresponding to each row of the silicon semiconductor detectors by sampling an electric signal outputted by each of the row signal output ends; an energy acquiring module coupled to the crystal position recognizing module and each of the samplers and configured to acquire energy of a sampled electric signal of a row including the silicon semiconductor detector corresponding to the crystal hit by a photon according to the position of the crystal hit by a photon and recognized by the crystal position recognizing module; and a valid event recognizing module coupled to the energy acquiring module and configured to recognize an event of hitting the crystal by a photon as a valid event when energy outputted by the energy acquiring module is within a preset energy range.

The apparatus can further include a plurality of amplifiers, wherein each of the amplifiers is respectively coupled between one of the row signal output ends and one of the samplers and configured to amplify an electric signal outputted by the one of the row signal output ends, and wherein each of the samplers is coupled to a respective one of the amplifiers and configured to obtain a sampled electric signal corresponding to a respective row of the silicon semiconductor detectors by sampling an electric signal amplified by the respective amplifiers.

The apparatus can also further include n time recording modules, wherein the n is an integer no less than 2, wherein the silicon semiconductor detector array is divided into n groups of silicon semiconductor detectors, the n time recording modules each corresponding to a respective one of the n groups of silicon semiconductor detectors, and wherein each of the time recording modules is coupled to each silicon semiconductor detector in a corresponding group of silicon semiconductor detectors and the valid event recognizing module and configured to record time of occurrence of a valid event recognized by the valid event recognizing module according to a voltage outputted by each of the silicon semiconductor detectors.

The apparatus can further include an OR logic module coupled to at least two of the row signal comparing modules and configured to carry out a logic OR operation on row comparison results outputted by the connected at least two row signal comparing modules to obtain a logic OR result; and a time recording module coupled to the OR logic module and the valid event recognizing module and configured to record time of occurrence of a valid event recognized by the valid event recognizing module according to a logic OR result outputted by the OR logic module.

In some implementations, the apparatus further includes a plurality of samplers, respectively connected to each of the column signal output ends and configured to obtain a sampled electric signal corresponding to each column of the silicon semiconductor detectors by sampling an electric signal outputted by each of the column signal output ends; an energy acquiring module coupled to the crystal position recognizing module and each of the samplers and configured to acquire an energy of a sampled electric signal of a column including the silicon semiconductor detector corresponding to the crystal hit by the photon according to the position of the crystal hit by the photon and recognized by the crystal position recognizing module; and a valid event recognizing module coupled to the energy acquiring module and configured to recognize an event of hitting the crystal by a photon as a valid event when the energy outputted by the energy acquiring module is within a preset energy range.

The apparatus can further include a plurality of amplifiers, wherein each of the amplifiers is respectively coupled between one of the column signal output ends and one of the samplers and configured to amplify an electric signal outputted by the one of the column signal output ends, and wherein each of the samplers is coupled to a respective one of the amplifiers and configured to obtain a sampled electric signal corresponding to a respective column of the silicon semiconductor detectors by sampling an electric signal amplified by the respective amplifiers.

The apparatus can further include n time recording modules, wherein the n is an integer no less than 2, wherein the silicon semiconductor detector array is divided into n groups of silicon semiconductor detectors, the n time recording modules each corresponding to a respective one of the n groups of silicon semiconductor detectors, and wherein each of the time recording modules is coupled to each silicon semiconductor detector in a corresponding group of silicon semiconductor detectors and the valid event recognizing module and configured to record time of occurrence of a valid event recognized by the valid event recognizing module according to a voltage outputted by each of the silicon semiconductor detectors.

The apparatus can further include an OR logic module coupled to at least two of the column signal comparing modules and configured to carry out a logic OR operation on column comparison results outputted by the connected at least two column signal comparing modules to obtain a logic OR result; and a time recording module coupled to the OR logic module and the valid event recognizing module and configured to record time of occurrence of a valid event recognized by the valid event recognizing module according to a logic OR result outputted by the OR logic module.

In some implementations, the apparatus further includes a plurality of integrating circuits each respectively coupled to a respective one of the row signal output ends and configured to integrate an electric signal outputted by the respective one of the row signal output ends; a plurality of peak holding circuits coupled to a respective one of the integrating circuits and configured to hold an electric signal outputted by the respective one of the integrating circuits at a peak; a multiplexer coupled to the crystal position recognizing module and each of the peak holding circuits and configured to: select a peak holding circuit of a row including the silicon semiconductor detector corresponding to the crystal hit by a photon from the plurality of peak holding circuits according to the position of the crystal hit by the photon in the crystal array and recognized by the crystal position recognizing module, and output an electric signal of the selected peak holding circuit; a sampling module coupled to the multiplexer and configured to obtain a sampled electric signal by sampling an electric signal outputted by the multiplexer; an energy acquiring module coupled to the crystal position recognizing module and the sampling module and configured to acquire energy of a sampled electric signal outputted by the sampling module and associate the acquired energy with the position of the crystal hit by a photon and recognized by the crystal position recognizing module; and a valid event recognizing module coupled to the energy acquiring module and configured to recognize an event of hitting the crystal by a photon as a valid event when energy outputted by the energy acquiring module is within a preset energy range.

The peak holding circuit can include an amplifier and a diode, and wherein: one input end of the amplifier is coupled to an output end of the integrating circuit, an output end of the amplifier is coupled to an anode of the diode, and a cathode of the diode is coupled to another input end of the amplifier and the multiplexer.

The apparatus can further include n time recording modules, wherein the n is an integer no less than 2, wherein the silicon semiconductor detector array is divided into n groups of silicon semiconductor detectors, the n time recording modules each corresponding to a respective one of the n groups of silicon semiconductor detectors, and each of the time recording modules is coupled to each silicon semiconductor detector in a corresponding group of silicon semiconductor detectors and the valid event recognizing module and configured to record time of occurrence of a valid event recognized by the valid event recognizing module according to a voltage outputted by each of the silicon semiconductor detectors.

The apparatus can further include an OR logic module coupled to at least two of the row signal comparing modules and configured to carry out a logic OR operation on row comparison results outputted by the connected at least two row signal comparing modules to obtain a logic OR result; and a time recording module coupled to the OR logic module and the valid event recognizing module and configured to record time of occurrence of a valid event recognized by the valid event recognizing module according to a logic OR result outputted by the OR logic module.

In some implementations, the apparatus further includes a plurality of integrating circuits each coupled to a respective one of the column signal output ends and configured to integrate an electric signal outputted by the respective one of the column signal output ends; a plurality of peak holding circuits each coupled to a respective one of the integrating circuits and configured to hold an electric signal outputted by the respective one of the integrating circuits at a peak; a multiplexer coupled to the crystal position recognizing module and each of the peak holding circuits and configured to: select a peak holding circuit of a column including the silicon semiconductor detectors corresponding to the crystal hit by a photon from the plurality of peak holding circuits according to the position of the crystal hit by the photon in the crystal array and recognized by the crystal position recognizing module, and output an electric signal of the selected peak holding circuit; a sampling module coupled to the multiplexer and configured to obtain a sampled electric signal by sampling an electric signal outputted by the multiplexer; an energy acquiring module coupled to the crystal position recognizing module and the sampling module and configured to acquire energy of a sampled electric signal outputted by the sampling module and associate the acquired energy with the position of the crystal hit by a photon and recognized by the crystal position recognizing module; and a valid event recognizing module coupled to the energy acquiring module and configured to recognize an event of hitting the crystal by a photon as a valid event when energy outputted by the energy acquiring module is within a preset energy range.

The peak holding circuit can include an amplifier and a diode, and wherein: an input end of the amplifier is coupled to an output end of the integrating circuit, an output end of the amplifier is coupled to an anode of the diode, and a cathode of the diode is coupled to another input end of the amplifier and the multiplexer.

The apparatus can further include n time recording modules, wherein the n is an integer no less than 2, wherein the silicon semiconductor detector array is divided into n groups of silicon semiconductor detectors, the n time recording modules each corresponding to a respective one of the n groups of silicon semiconductor detectors, and wherein each of the time recording modules is coupled to each silicon semiconductor detector in a corresponding group of silicon semiconductor detectors and the valid event recognizing module and configured to record time of occurrence of a valid event recognized by the valid event recognizing module according to a voltage outputted by each of the silicon semiconductor detectors.

The apparatus can further include an OR logic module coupled to at least two of the column signal comparing modules and configured to carry out a logic OR operation on column comparison results outputted by the connected at least two column signal comparing modules to obtain a logic OR result; and a time recording module coupled to the OR logic module and the valid event recognizing module and configured to record time of occurrence of a valid event recognized by the valid event recognizing module according to a logic OR result outputted by the OR logic module.

The details of one or more embodiments of the subject matter described in the present disclosure are set forth in the accompanying drawings and description below. Other features, aspects, and advantages of the subject matter will become apparent from the description, the drawings, and the claims.

BRIEF DESCRIPTION OF DRAWINGS

Features of the present disclosure are illustrated by way of example and not limited in the following figures, in which like numerals indicate like elements.

DETAILED DESCRIPTION

To reduce an energy error in a PMT-based photoelectric detection, a silicon semiconductor detector may be employed to replace a photomultiplier tube, and each silicon semiconductor detector may correspond to one crystal. In such a case, to recognize a position of each crystal, each silicon semiconductor detector may likely need to be connected to a circuit formed by elements such as an amplifier and a comparator, etc.

Figure 1:
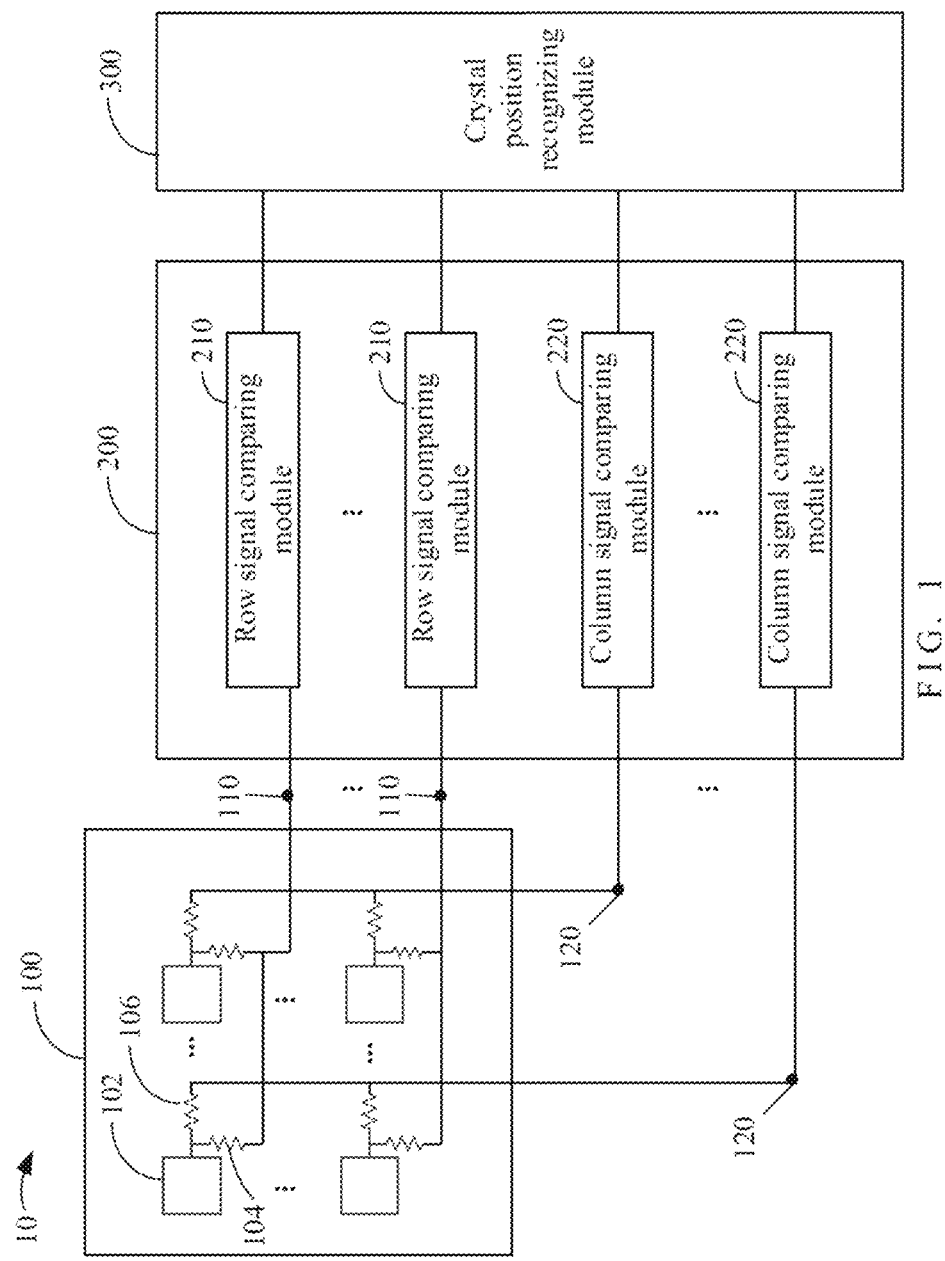
FIG. 1 is a schematic hardware diagram of an apparatus for recognizing a position of a crystal in a nuclear detector according to an example of the present disclosure.

Referring to FIG. 1, an apparatus 10 for recognizing a position of a crystal in a nuclear detector provided by this example may include a silicon semiconductor detector array 100, wherein the silicon semiconductor detector array 100 may include a plurality of silicon semiconductor detectors 102. Each row of the silicon semiconductor detector array 100 may have a row signal output end 110, each column of the silicon semiconductor detector array 100 may have a column signal output end 120. Each of the silicon semiconductor detectors may be connected via a resistor 104 to a row signal output end 110 corresponding to a row including the silicon semiconductor detector, and may be connected via another resistor 106 to a column signal output end 120 corresponding to a column including the silicon semiconductor detector.

The apparatus 10 may further include a row and column signal processing module 200, the row and column signal processing module 200 may include a row signal comparing module 210 and a column signal comparing module 220, a row signal output end 110 for each row in the silicon semiconductor detector array 100 may be correspondingly connected to the row signal comparing module 210, and a column signal output end 120 for each column in the silicon semiconductor detector array 100 may be correspondingly connected to the column signal comparing module 220.

The row signal comparing module 210 may be configured to compare the sum of voltages outputted by a corresponding row of silicon semiconductor detectors with a threshold voltage to obtain a row comparison result. For example, the threshold voltage may be a value in a range from 20 mv to 30 mv.

The column signal comparing module 220 may be configured to compare the sum of voltages outputted by a corresponding column of silicon semiconductor detectors with the threshold voltage to obtain a column comparison result. The threshold voltage for the column signal comparing module 220 may be the same as the threshold voltage for the row signal comparing module 210.

The apparatus 10 may further include a crystal position recognizing module 300, wherein the crystal position recognizing module 300 may be respectively connected to the row signal comparing module 210 and the column signal comparing module 220 and configured to recognize a position of a crystal hit by a photon according to the row comparison result outputted by each row signal comparing module 210 and the column comparison result outputted by each column signal comparing module 220.

Figure 2:
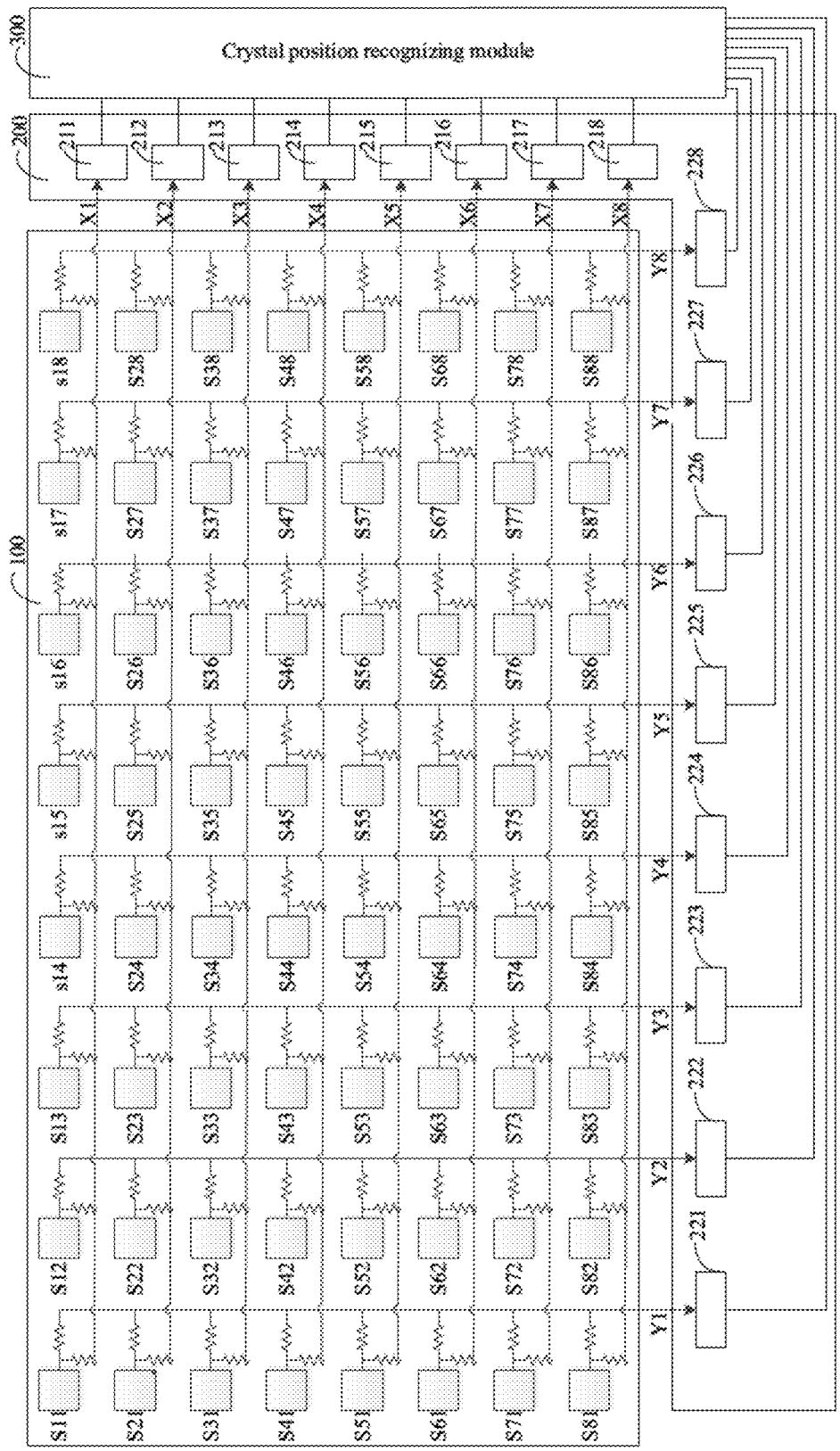
FIG. 2 is a schematic diagram of an 8×8 silicon semiconductor detector array in an apparatus for recognizing a position of a crystal in a nuclear detector according to an example of the present disclosure.

A working principle of the apparatus 10 for recognizing a position of a crystal in a nuclear detector is introduced in the following by taking an 8×8 silicon semiconductor detector array as an example. Referring to FIG. 2, in which a silicon semiconductor detector S11 is connected via a first resistor with a row signal comparing module 211 and is connected via a second resistor with a column signal comparing module 221. The first resistor and the second resistor may have the same resistance. In a particular example, the first resistor and the second resistor each have a resistance of 22 Ohms. In some cases, the silicon semiconductor detector S11 may be connected to the row signal comparing module 211 or the column signal comparing module 211 via a diode or any suitable combination of a resistor, a diode, or any other electronic device. Other silicon semiconductor detectors may be connected with corresponding row signal comparing modules and column signal comparing modules in a similar way to the silicon semiconductor detector S11.

When a crystal corresponding to the silicon semiconductor detector S11 is hit by a photon, the silicon semiconductor detector S11 may convert visible light generated by the crystal into an electric signal. Due to an existence of resistance, e.g., the first resistor, an electric potential difference may be generated between the silicon semiconductor detector S11 and the row signal comparing module 211, and the silicon semiconductor detector S11 may transmit a generated electric signal to the row signal comparing module 211. Meanwhile, due to the existence of resistance, e.g., the second resistor, an electric potential difference may be generated between the silicon semiconductor detector S11 and the corresponding column signal comparing module 221, and the silicon semiconductor detector S11 may also transmit the converted electric signal to the column signal comparing module 221.

Since the row signal comparing module 211 may be connected to the silicon semiconductor detectors S11, S12, S13, S14, S15, S16, S17 and S18 through one bus X1, what is received by the row signal comparing module 211 is a superposed electric signal from the bus X1. The row signal comparing module 211 may obtain the sum of voltages outputted by this row of eight silicon semiconductor detectors according to the superposed electric signal. In practical applications, even though none of crystals corresponding to the row of silicon semiconductor detectors is hit by a photon, weak current may also likely flow through the bus X1, therefore the row signal comparing module 211 may also receive an electric signal. To relatively accurately recognize a position of a crystal hit by a photon, in this example, the row signal comparing module 211 may compare the sum of voltages outputted by the row of silicon semiconductor detectors with a threshold voltage, e.g., the row signal comparing module 211 may compare a voltage value corresponding to the received electric signal from the bus X1 with the threshold voltage to obtain the row comparison result.

The present disclosure does not limit a hardware implementation of the row signal comparing module 211. In an example, a processor may be employed for the comparing and calculating operations. In another example, a comparator may also be employed for the comparing operation, e.g., the superposed electric signal and a threshold voltage signal may be used as an input of the comparator. A high level may be outputted if the sum of voltages outputted by the row of silicon semiconductor detectors is greater than or equal to (or no less than) the threshold voltage; and a low level or no level may be outputted if the sum of voltages outputted by the row of silicon semiconductor detectors is less than the threshold voltage.

Figure 3:
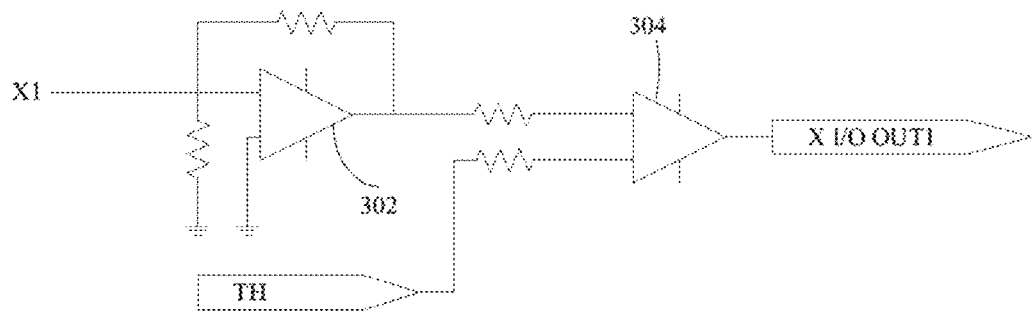
FIG. 3A is a schematic diagram of a row signal comparing module in an apparatus for recognizing a position of a crystal in a nuclear detector according to an example of the present disclosure.
FIG. 3B is a schematic diagram of a column signal comparing module in an apparatus for recognizing a position of a crystal in a nuclear detector according to an example of the present disclosure.
Figure 3:
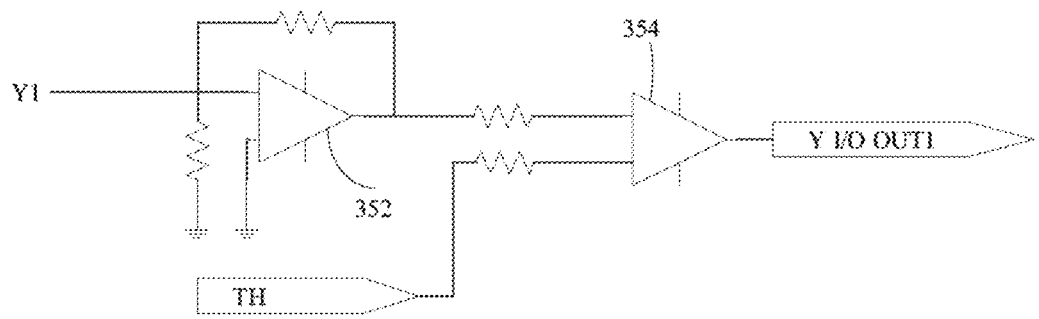

In some implementations, the apparatus may further include an amplifier 302, as illustrated in FIG. 3A. The amplifier 302 is used for amplifying an electric signal from the bus X1 and then outputting the amplified electric signal into the comparator 304 for the comparing operation. The working principle of other row signal comparing modules is the same as that of the row signal comparing module 211.

Referring back to FIG. 2, similarly, since the column signal comparing module 221 may be connected to the silicon semiconductor detectors S11, S21, S31, S41, S51, S61, S71 and S81 through one bus Y1, what is received by the column signal comparing module 221 is a superposed electric signal from the bus Y1. The column signal comparing module 221 may obtain the sum of voltages outputted by this column of eight silicon semiconductor detectors according to the superposed electric signal. In practical application, in the case that none of crystals corresponding to the column of silicon semiconductor detectors is hit by a photon, weak current may likely flow through the bus, therefore the column signal comparing module 221 may also receive an electric signal. To relatively accurate recognize a position of a crystal hit by a photon, in this example, the column signal comparing module 221 may compare the sum of voltages outputted by the column of silicon semiconductor detectors with the threshold voltage, e.g., the column signal comparing module 221 may compare a voltage value corresponding to the received electric signal from the bus Y1 with the threshold voltage to obtain the column comparison result.

The present disclosure does not limit a hardware implementation of the column signal comparing module 221. For example, in an example, a processor may be employed for the comparing and calculating operations. In another example, a comparator may also be employed for the comparing operation, e.g., a high level may be outputted if the sum of voltages outputted by the column of silicon semiconductor detectors is greater than or equal to (or no less than) the threshold voltage 20-30 mv; and a low level may be outputted or no level may be outputted if the sum of voltages outputted by the column of silicon semiconductor detectors is less than the threshold voltage.

In some implementations, the apparatus may further include an amplifier 352, as illustrated in FIG. 3B. The amplifier 352 is configured to amplify an electric signal from the bus Y1 and then input the amplified electric signal into the comparator 354 for the comparing operation. The working principle of other column signal comparing modules is the same as that of the column signal comparing module 221.

The row signal comparing modules 211-218 and the column signal comparing modules 221-228 may be connected with a crystal position recognizing module 300. After reading row comparison results respectively sent by the row signal comparing modules 211-218 and column comparison results respectively sent by the column signal comparing modules 221-228, the crystal position recognizing module 300 may recognize a position of a crystal hit by a photon according to the eight row comparison results and the eight column comparison results.

The recognition of the position of the crystal is not limited in the present disclosure. For example, supposing values outputted by each row signal comparing module and each column signal comparing module are level values, e.g., a high level may be outputted if the sum of voltages outputted by a row (or column) of silicon semiconductor detectors is greater than or equal to the threshold voltage; and a low level may be outputted or no level may be outputted if the sum of voltages outputted by a row (or column) silicon semiconductor detectors is less than the threshold voltage. If both a row comparison result and a column comparison result are high levels, an intersection point of a row of silicon semiconductor detectors corresponding to the row comparison result and a column of silicon semiconductor detectors corresponding to the column comparison result may be recognized to be the position of a crystal hit by a photon.

For example, in FIG. 2, suppose the row comparison result outputted by the row signal comparing module 215 is a high level and the column comparison result outputted by the column signal comparing module 223 is also a high level, an intersection point of a row of silicon semiconductor detectors corresponding to the row signal comparing module 215 and a column of silicon semiconductor detectors corresponding to the column signal comparing module 223 is a silicon semiconductor detector S53. Therefore, a crystal corresponding to the position of the silicon semiconductor detector S53 may be recognized to be hit by a photon.

The present disclosure does not limit a hardware implementation of the crystal position recognizing module 300, which may be, for example, a processor or a field programmable gate array (FPGA), etc.

In addition, in the present disclosure, the silicon semiconductor detector may be any photoelectric detector based on a silicon semiconductor, for example, a silicon photomultiplier (SiPM) or the like, which is not specifically limited in the present disclosure. The present disclosure does not limit a type of a crystal corresponding to the silicon semiconductor detector, which may be, for example, BGO (Bismuth Germanium Oxide), LYSO (Lutetium-yttrium oxyorthosillicate) and LSO (Lutetium oxyorthosillicate), etc.

In this example, each row of silicon semiconductor detectors in the silicon semiconductor detector array may correspond to one row signal comparing module, and each column of silicon semiconductor detectors in the silicon semiconductor detector array may correspond to one column signal comparing module. The crystal position recognizing module may be connected to each of the row signal comparing modules and each of the column signal comparing modules and configured to recognize a position of a crystal hit by a photon according to the row comparison result outputted by each of the row signal comparing modules and the column comparison result outputted by each of the column signal comparing modules. Thus, to an 8×8 silicon semiconductor detector array, recognition of a crystal position may be implemented only by eight row signal comparing modules and eight column signal comparing modules with the addition of a crystal position recognizing module. Therefore, compared with a case where each silicon semiconductor detector in a silicon semiconductor detector array is connected to an amplifier and a comparator, in this example, quantity and cost of required hardware may be greatly reduced, and a system scale may also be effectively reduced.

In a nuclear detector imaging system, radioactive biological tracer drugs may be first rejected into a subject, for example, 13N—NH, 18F-FDOPA, 18F-FDG, 11C-Acetate, 15O—H2O and so on, and these drugs may be synthesized by radionuclides that may release positrons. Generally biological tracer drugs are proton-rich nuclides, which may generate positrons in a decay process, and generally positron (β+) decay occurs in artificial radionuclides. A positron emitted by a radionuclide injected into a human body may combine, after moving about 1 mm in the human body, with a negatron in the human body to produce annihilation radiation, wherein two γ photons having the same energy (about 511 keV) and in opposite directions may be generated during an annihilation of the positron and the negatron. Generally, an event of occurrence of an annihilation reaction of a pair of electrons is referred to as a single event.

As previously mentioned, in ideal conditions, each photon has an energy of about 511 keV. Some energy may likely be lost when a photon moves in a human body or hits a crystal, or a crystal hit by a photon may receive energy scattered by other photons. Therefore, the energy value of an electric signal actually converted by the silicon semiconductor detector may likely fluctuate around 511 keV. An energy range may be preset or predetermined in this example. An event of hitting a crystal by a photon may be considered to be a valid event if the energy of an electric signal generated by the crystal hit by a photon is within a preset energy range (e.g., 400 keV-600 keV), and the event may be considered to be an invalid event if the energy is beyond the preset energy range. Only a valid event may participate in subsequent processing.

Figure 4:
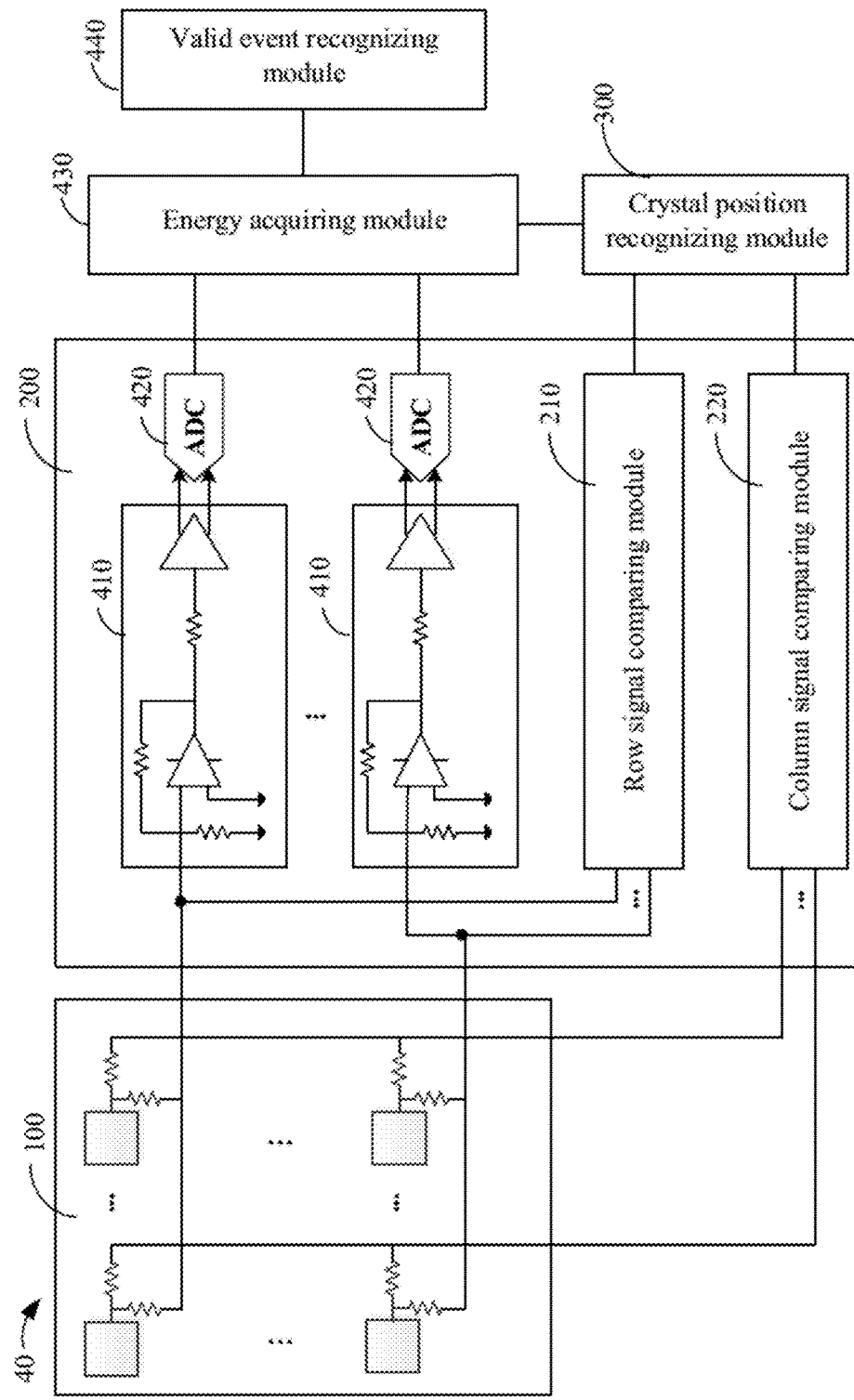
FIG. 4 is a schematic hardware diagram of an apparatus for recognizing a position of a crystal in a nuclear detector according to another example of the present disclosure.

FIG. 4 schematically illustrates a structure diagram of an apparatus 40 for recognizing a position of a crystal in a nuclear detector according to another example of the present disclosure. Referring to FIG. 4, on a basis of the example as shown in FIG. 1, a row and column signal processing module 200 of the apparatus 40 for recognizing a position of a crystal in a nuclear detector may further include an amplifier 410 and a sampler 420. For example, each row or column of silicon semiconductor detectors may correspond to one amplifier 410 and one sampler 420. The amplifier 410 may be configured to amplify an electric signal outputted by a corresponding row or column of silicon semiconductor detectors, and the sampler 420 may be configured to sample an electric signal amplified by the amplifier 410. As an example, FIG. 4 illustrates a case where each row of silicon semiconductor detectors may correspond to one amplifier 410 and one sampler 420. As shown in FIG. 4, the sampler 420 may be implemented by an analog-to-digital converter (ADC), wherein the ADC may be configured to sample an amplified electric signal, for example, 10 ns/time.

The apparatus 40 may further include an energy acquiring module 430 and a valid event recognizing module 440. The sampler 420 may be connected to the energy acquiring module 430, the energy acquiring module 430 may be connected to the crystal position recognizing module 300, and the valid event recognizing module 440 may be connected to the energy acquiring module 430.

The energy acquiring module 430 may be configured to acquire, according to the position of the crystal hit by a photon, a sampled electric signal of a row or column including the silicon semiconductor detector corresponding to the crystal, and calculate and obtain the energy of the sampled electric signal. How to calculate and obtain energy according to an electric signal is common knowledge to those skilled in the art, which is thus not necessarily described any more herein.

The valid event recognizing module 440 is configured to determine whether the energy is within the preset energy range and recognize an event of hitting the crystal by a photon as a valid event when the energy is within the preset energy range.

It is to be noted that in this example a total energy of a row (or column) including a crystal hit by a photon may be taken as an energy produced by the crystal hit by a photon. This is because in practical applications, only one row (or column) of crystals may likely be hit within a time range (for example, 100 ns) under normal circumstances. In other words, a probability of two or more than two crystals of one row (or column) of crystals being hit by photons within a time range is very small. If this case occurs, the crystals may be unable to participate in determining a coincidence event because energy of the crystals in this row (or column) goes beyond the preset energy range. Therefore, screening by utilizing the energy range may ensure such a valid event where merely one crystal among a row (or column) of crystals participating in determining a coincidence event is hit by a photon within a time range.

In this example, amplifiers and samplers may be disposed by taking a row or column as a unit based on a principle that merely one crystal among a row (or column) of crystals may likely be hit within a time range (e.g., 100 ns) generally. For example, an 8×8 silicon semiconductor detector array may only need eight amplifiers and eight samplers. Thus, compared with a case where each silicon semiconductor detector in a silicon semiconductor detector array may correspond to one amplifier and one sampler, in this example, the quantity of hardware may be greatly reduced, and thus the cost may be effectively reduced and a system scale may be downsized.

In addition, the present disclosure does not limit specific hardware implementation manners of the energy acquiring module 430 and the valid event recognizing module 440. For example, in an example, functions of the two modules may be executed by a processor. In another example, functions of the two modules may be executed by an FPGA. In addition, the energy acquiring module 430, the valid event recognizing module 440, and the crystal position recognizing module 300 may use the same device or different devices, which is not limited in the present disclosure.

Figure 5:
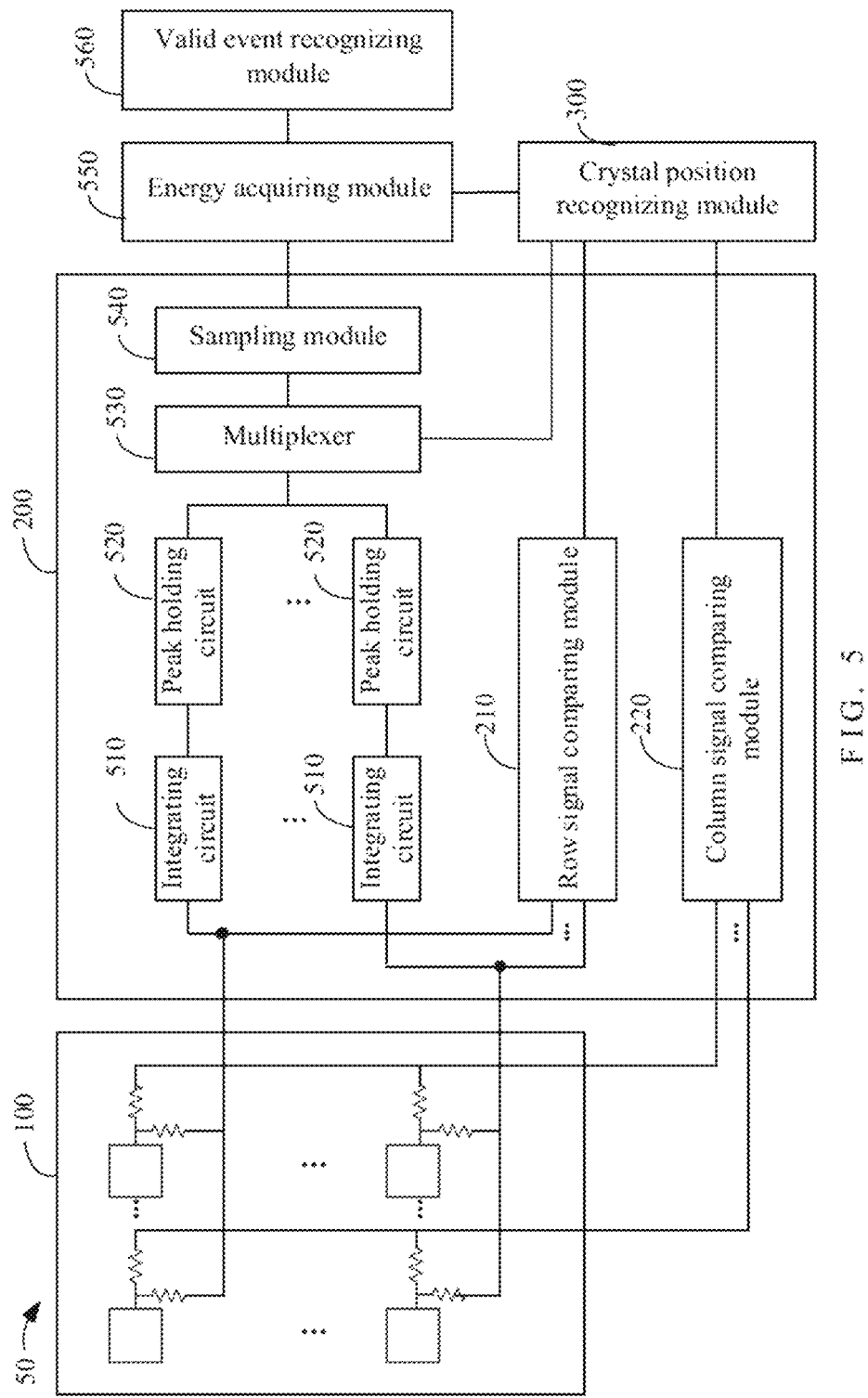
FIG. 5 is a schematic hardware diagram of an apparatus for recognizing a position of a crystal in a nuclear detector according to a third example of the present disclosure.

FIG. 5 illustrates an apparatus 50 for recognizing a position of a crystal in a nuclear detector according to another example of the present disclosure. Referring to FIG. 5, on the basis of the example as shown in FIG. 1, a row and column signal processing module 200 of the apparatus 50 for recognizing a position of a crystal in a nuclear detector may further include an integrating circuit 510, a peak holding circuit 520, a multiplexer 530, and/or a sampling module 540. The apparatus may further include an energy acquiring module 550 and/or a valid event recognizing module 560. FIG. 5 illustrates a case where each row of silicon semiconductor detectors may correspond to one integrating circuit 510 and one peak holding circuit 520. In some cases, each column of silicon semiconductor detectors may correspond to one integrating circuit and one peak holding circuit.

An input end of the integrating circuit 510 may be correspondingly connected to the row signal output end or the column signal output end of the semiconductor detector array. For illustration only, FIG. 5 illustrates a case where the integrating circuit 510 may be connected to the row signal output end. An output end of the integrating circuit 510 may be correspondingly connected to an input end of the peak holding circuit 520. An output end of the peak holding circuit 520 may be connected to the multiplexer 530. The multiplexer 530 may be connected to the sampling module 540 and the crystal position recognizing module 300. The sampling module 540 may be connected to the energy acquiring module 550, and the energy acquiring module 550 may be connected to a valid event recognizing module 560.

The integrating circuit 510 is configured to integrate an electric signal outputted by the row signal output end or the column signal output end of the semiconductor detector array.

Since performing an energy calculation according to an electric signal in essence is to integrate the electric signal, in this example, an electric signal outputted by the row signal output end or the column signal output end of the semiconductor detector array may be integrated by the integrating circuit 510 so that the peak holding circuit 520 may hold the integrated electric signal at a peak to be output, wherein the peak may represent the energy value of an event.

The present disclosure does not limit a hardware implementation of the integrating circuit 510. For example, in an example, the integrating circuit 510 may be an integrating amplifier; and in another example, the integrating circuit 510 may be a proportion integration differentiation (PID) control circuit.

Since a time duration of a section of an electric signal generated by a crystal hit by a photon is very short and is nearly transient, it is needed to hold the section of the electric signal in some way to avoid outputting the section of the electric signal before acquiring the position of the crystal. Therefore, the output end of the integrating circuit 510 may be correspondingly connected to the input end of the peak holding circuit 520. The peak holding circuit 520 is configured to hold an electric signal outputted by the integrating circuit at a peak.

Figure 6A:
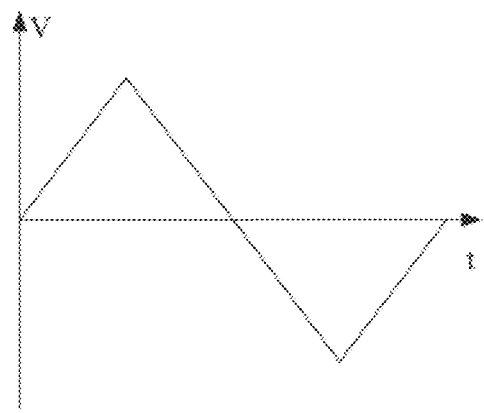
FIG. 6A is a schematic diagram of an electric signal before peak holding in an apparatus for recognizing a position of a crystal in a nuclear detector according to a fourth example of the present disclosure.
Figure 6B:
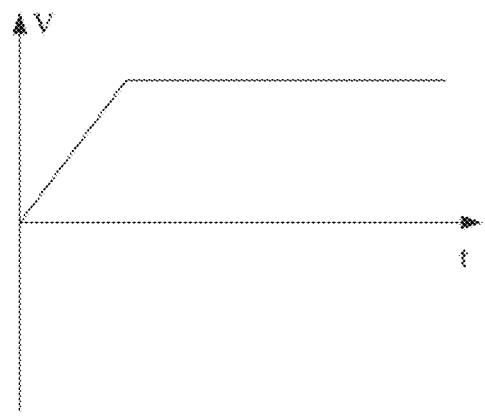
FIG. 6B is a schematic diagram of an electric signal after peak holding in an apparatus for recognizing a position of a crystal in a nuclear detector according to a fifth example of the present disclosure.

The so-called "peak holding" may be simply interpreted as holding an electric signal at a peak and actually may be to output a peak of the electric signal. Referring to FIG. 6A and FIG. 6B, FIG. 6A is an electric signal before peak holding and its waveform is a triangular wave; FIG. 6B is an electric signal after peak holding, e.g., the electric signal is held at a peak to be output when the electric signal reaches the peak.

Figure 7:
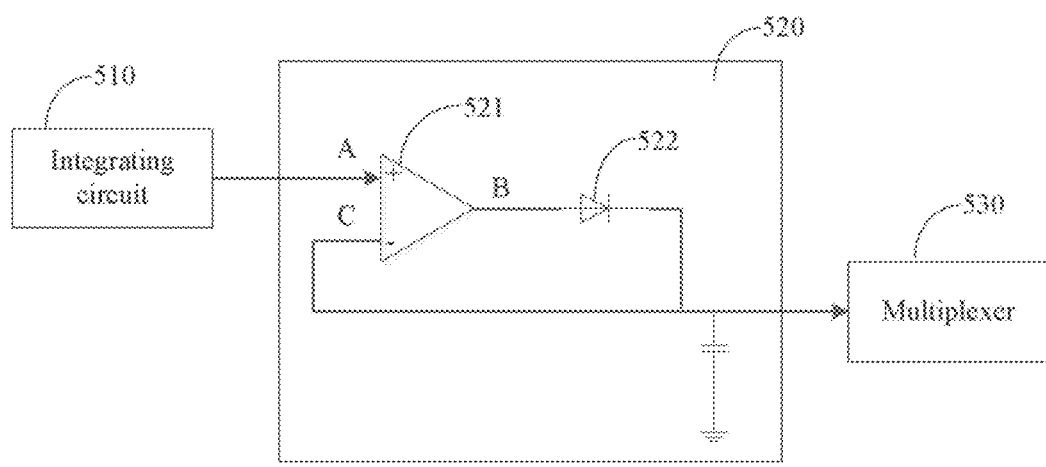
FIG. 7 is a schematic diagram of a peak holding circuit in an apparatus for recognizing a position of a crystal in a nuclear detector according to a sixth example of the present disclosure.

The present disclosure does not limit a specific hardware implementation of the peak holding circuit 520. In an example, the peak holding circuit 520 may include an amplifier 521 and a diode 522, as illustrated in FIG. 7. One input end of the amplifier 521 may be connected to the output end of the integrating circuit 510, an output end of the amplifier 521 may be connected to an anode of the diode 522, a cathode of the diode 522 may be connected to another input end of the amplifier 521, and the cathode of the diode 522 may be also connected to the multiplexer 530.

The working principle of the peak holding circuit 520 is as below: when an electric signal is inputted from a first input end (Point A) of the amplifier 521, in a signal increasing process, a voltage of the output end (Point B) of the amplifier 521 may increase as a voltage of the Point A increases, and a voltage of a second input end (Point C) of the amplifier 521 may also increase accordingly because at the moment the diode 522 is in an "on" state. After reaching a maximum value, the voltage of the Point A may start dropping, in a signal dropping process, the voltage of the Point B may also drop accordingly. However, since the voltage of the Point C is higher than that of the Point B, which may cause cut-off of the diode 522, and at this moment the voltage of the Point C may be held at the maximum voltage value. Therefore, a voltage value of an electric signal subsequently outputted to the multiplexer 530 may be held at a voltage peak.

In addition, the peak holding circuit 520 of the present disclosure may further include a quick bleed-off circuit. In this way, after completion of sampling, the bleed-off circuit may be controlled by means of a control signal so that the peak holding circuit 520 may be recovered to a before-holding state to wait for advent of a next signal. The present disclosure does not limit implementation of the bleed-off circuit.

Referring back to FIG. 5, the crystal position recognizing module 300 may be connected to the multiplexer 530 and may control on/off of the multiplexer 530 according to the position of a crystal hit by a photon. An output end of the peak holding circuit 520 may be connected to the multiplexer 530. Thus, the multiplexer 530 may be configured to select out an electric signal outputted by the peak holding circuit 520 corresponding to the position of a crystal hit by a photon in the crystal array. The position may be recognized by the crystal position recognizing module 300. The multiplexer 530 may output the selected electric signal to the sampling module 540.

The multiplexer refers to an apparatus selecting simplex electric signal from multiplex electric signals for outputting, and hardware thereof may be implemented by means of an analog switch, an FPGA and so on, which is not specifically limited in the present disclosure. In this example, the crystal position recognizing module 300 may control the multiplexer 530 to select out an electric signal corresponding to a crystal from electric signals outputted by the peak holding circuit 520 according to the position of the crystal hit by a photon in the crystal array, and to output the selected electric signal to the sampling module 540. An example is taken where the multiplexer 530 includes a plurality of analog switches, wherein each analog switch has a corresponding number. For example, in the case that crystals are encoded according to positions of the crystals in the crystal array, an encoding of an analog switch corresponding to one crystal may be the same as that of the crystal. Generally, all the analog switches are in an "off" state. When the position of a crystal hit by a photon is recognized by the crystal position recognizing module 300, the multiplexer 530 may control an analog switch corresponding to the crystal to be turned on according to an encoding corresponding to the crystal, thereby outputting an electric signal subjected to peak holding and corresponding to the crystal.

The multiplexer 530 may be connected to the sampling module 540, and the sampling module 540 may be configured to sample an electric signal outputted by the multiplexer 530.

The present disclosure does not limit hardware implementation of the sampling module 540, which may be, for example, an analog-to-digital converter (ADC) device.

The sampling module 540 may be connected to the energy acquiring module 550, and the energy acquiring module 550 may be configured to acquire energy generated by the crystal hit by a photon by calculating the sampled electric signal. In this way, recognition of a valid event may be carried out on the basis of energy calculated by the energy acquiring module 550 subsequently. An electric signal inputted into the sampling module 540 is an electric signal subjected to "peak holding", which may be deemed to be a signal obtained after integrating an original signal. Therefore, energy generated by a crystal hit by a photon may be acquired by reading a voltage of an output signal of the sampling module 540 and performing an energy conversion on the voltage. It may be determined whether energy calculated by the energy acquiring module 550 is within a preset energy range by connecting the valid event recognizing module 560 with the energy acquiring module 550. The event may be considered to be a valid event if the energy is within the preset energy range. In this way, recognition of a valid event may be implemented.

Functions of the energy acquiring module 550 and the valid event recognizing module 560 may be implemented by means of hardware such as a field programmable gate array (FPGA) or a processor, which is not specifically limited by the present disclosure. The crystal position recognizing module 300, the energy acquiring module 550 and the valid event recognizing module 560 may be implemented in one or more devices, which is not specifically limited in the present disclosure.

A basic principle of the valid event recognizing apparatus provided in this example is to add the multiplexer 530 so as to select out a simplex electric signal corresponding to a crystal hit by a photon from a plurality of electric signals for acquiring energy. Therefore, the whole circuit may only include one sampling module 540, and thus the quantity of sampling modules may be greatly reduced and cost may be effectively reduced.

A time recording may be performed on a valid event after recognizing the position of a crystal hit by a photon and obtaining the energy of the valid event.

Determining a coincidence event refers to determining a difference in time of arrival of photons. When the time difference is less than a preset time window (e.g., 3 ns~4.5 ns), the valid event may be determined to be a coincidence event. Therefore, a basis of determining a coincidence event is to carry out a time recording, e.g., a moment when a valid event occurs may be recognized. According to one example, an apparatus for recognizing a position of a crystal in a nuclear detector may further include n time recording modules, wherein the n is an integer greater than or equal to 2. Correspondingly, the silicon semiconductor detector array may be divided into n groups of silicon semiconductor detectors, the n time recording modules may one to one correspond to the n groups of silicon semiconductor detectors, and each silicon semiconductor detector in one group may be connected to a corresponding time recording module. In such a case, each of the time recording modules may utilize signals outputted by a corresponding group of silicon semiconductor detectors to record time when a valid event occurs in this group of silicon semiconductor detectors.

The present disclosure does not limit hardware implementation of the time recording module. For example, in an example, the time recording module may be a processor. In another example, the time recording module may be a time to digital converter (TDC). Time recording belongs to common knowledge widely known to those skilled in the art, which is thus not necessarily described any more herein.

Figure 8:
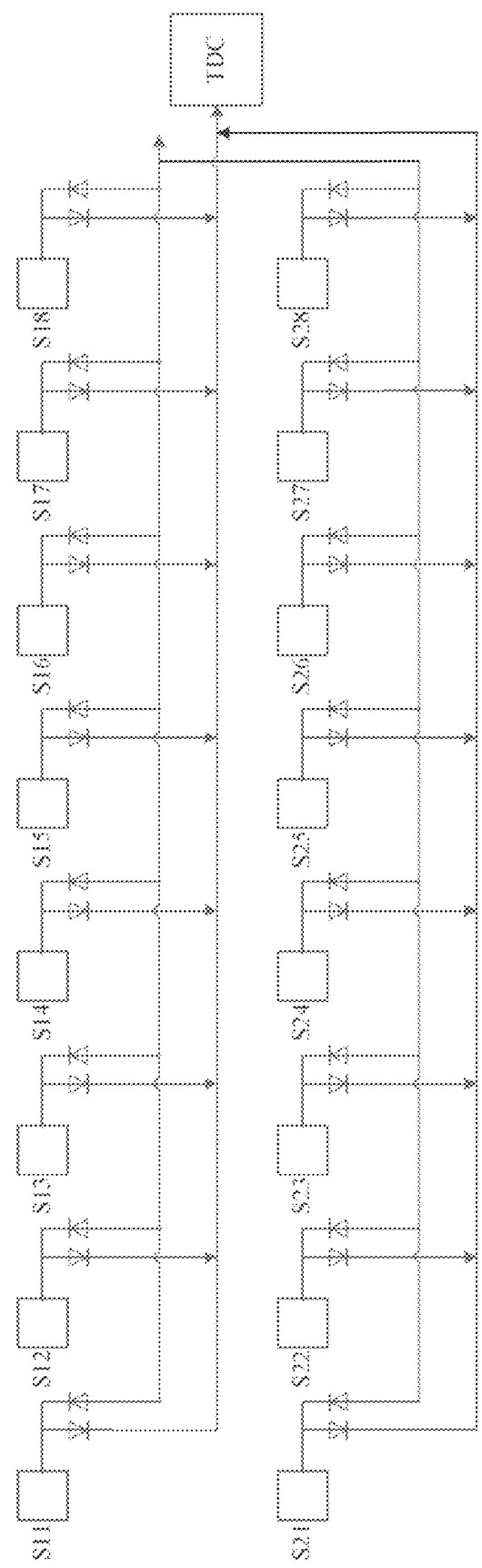
FIG. 8 is a schematic hardware diagram of a time recording in an apparatus for recognizing a position of a crystal in a nuclear detector according to a seventh example of the present disclosure.

In this example, the silicon semiconductor detector array may be divided into n groups, wherein each group may be connected to a time recording module so that the time recording module may record time of an event occurring in a corresponding group of silicon semiconductor detectors. Taking an 8×8 silicon semiconductor detector array as shown in FIG. 2 as an example, all silicon semiconductor detectors in the 8×8 silicon semiconductor detector array may be divided into four groups, and each group may correspond to one TDC. FIG. 8 is a schematic diagram of a relation of connection between a group of silicon semiconductor detectors and a TDC. In FIG. 8, one TDC may be in charge of performing a time recording on in total 16 silicon semiconductor detectors in two adjacent rows. Thus, the 8×8 silicon semiconductor detector array may only need four TDCs to complete time recording of all the silicon semiconductor detectors. Therefore, compared with a case where each silicon semiconductor detector in a silicon semiconductor detector array is connected to a time recording module, in this example, quantity of hardware may be greatly reduced, and thus cost may be effectively reduced and a system scale may be downsized.

According to one example, an apparatus for recognizing a position of a crystal in a nuclear detector provided by the present disclosure may further include an OR logic module and a time recording module. An input end of the OR logic module may be connected to at least two row comparison results of the silicon semiconductor detector array or at least two column comparison results of the silicon semiconductor detector array so as to execute an "OR" operation on the at least two row comparison results or column comparison results of the silicon semiconductor detector array. After executing the "OR" operation, the original at least two signals may be changed into one signal to be output, thus the quantity of time recording modules may be reduced and cost may be effectively reduced.

Figure 9:
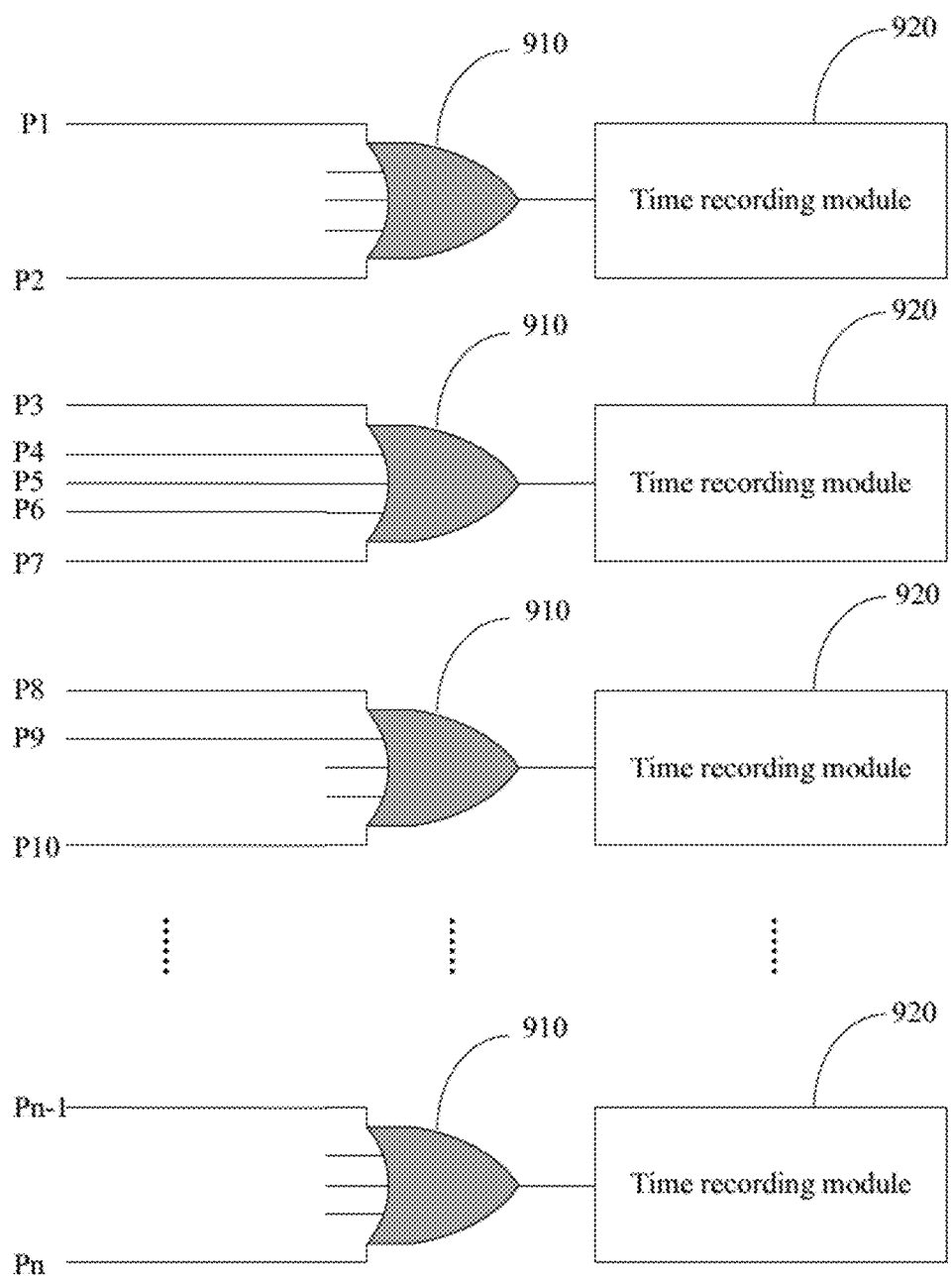
FIG. 9 is a schematic hardware diagram of a time recording in an apparatus for recognizing a position of a crystal in a nuclear detector according to an eighth example of the present disclosure.

FIG. 9 illustrates a schematic diagram of a relation of connection of at least two row comparison results of the silicon semiconductor detector array being inputted into one OR logic module. As shown in FIG. 9, the input end of each OR logic module 910 may be connected to at least two row comparison results or column comparison results P1-Pn of the silicon semiconductor detector array, and an output end of each OR logic module 910 may be connected to an input end of one time recording module 920.

Generally, at the same moment, one crystal array may be hit by one photon merely. Correspondingly, at the same moment, merely one row signal output end (or a column signal output end) of all row signal output ends (or column signal output ends) of the silicon semiconductor detector array may output a signal. Thus merely one row comparison result (or column comparison result) may be outputted. For example, in FIG. 9, if a crystal hit by a photon corresponds to a row comparison result P1, the row comparison result P1 may be inputted into a corresponding OR logic module 910, and a row comparison result P2 and the row comparison result P1 may be connected to the same OR logic module 910. Since a crystal corresponding to the row comparison result P2 is not hit by a photon and the row comparison result P2 is a low level or a zero level, an electric signal outputted by the OR logic module 910 in essence is an output of the row comparison result P1.

In this example, the quantity of row comparison results (or column comparison results) connected to the input end of the OR logic module 910 at least may be two and at most may be equal to the number of rows (or columns) of the silicon semiconductor detector array.

The output end of the OR logic module 910 may be connected to the time recording module 920. The time recording module 920 may utilize a row comparison result (or a column comparison result) for which an "OR" operation is executed to record time of occurrence of a valid event.

If a valid event is recognized, time recorded by the time recording module 920 corresponding to the valid event may be read so as to determine a coincidence event according to the time of occurrence of the valid event.

In this example, the input end of each OR logic module 910 may be connected to at least two row comparison results or column comparison results of the silicon semiconductor detector array, which may ensure the quantity of the OR logic modules 910 is less than the number of rows or columns of the silicon semiconductor detector array. In addition, one OR logic module 910 may be connected to one time recording module 920. In other words, the quantity of the time recording modules 920 may be equal to that of the OR logic modules 910. Therefore, compared with a case where each silicon semiconductor detector in a silicon semiconductor detector array may be connected to a time recording module, in this example, the quantity of the time recording modules 920 may be reduced, and thus hardware cost may be effectively reduced and a system scale may be downsized.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

For simplicity and illustrative purposes, the present disclosure is described by referring mainly to an example thereof. In the above description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

As used herein, the terms "a" and "an" are intended to denote at least one of a particular element, the term "includes" means includes but not limited to, the term "including" means including but not limited to, and the term "based on" means based at least in part on. Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive. Accordingly, other embodiments are within the scope of the following claims.

The invention claimed is:

1. An apparatus for recognizing a position of a crystal in a nuclear detector, comprising:
   a silicon semiconductor detector array, comprising a plurality of silicon semiconductor detectors arranged in a form of a crystal array in the nuclear detector, wherein:
   each row of the silicon semiconductor detector array is configured to output a sum of voltages outputted by the silicon semiconductor detectors in the row at a row signal output end,
   each column of the silicon semiconductor detector array is configured to output a sum of voltages outputted by the silicon semiconductor detectors in the column at a column signal output end,
   each of the silicon semiconductor detectors corresponds to a crystal in the crystal array and is coupled to a row signal output end of a row including the silicon semiconductor detector and to a column signal output end of a column including the silicon semiconductor detector;
   a plurality of row signal comparing modules each coupled to a respective row signal output end of a respective row of the silicon semiconductor detectors and configured to obtain a row comparison result corresponding to the respective row of the silicon semiconductor detectors by comparing a voltage on the respective row signal output end with a threshold voltage;
   a plurality of column signal comparing modules each coupled to a respective column signal output end of a respective column of the silicon semiconductor detector and configured to obtain a column comparison result corresponding to the respective column of the silicon semiconductor detectors by comparing a voltage on the respective column signal output end with the threshold voltage; and
   a crystal position recognizing module coupled to each of the row signal comparing modules and each of the column signal comparing modules and configured to recognize a position of a crystal hit by a photon according to row comparison results outputted by the row signal comparing modules and column comparison results outputted by the column signal comparing modules.

2. The apparatus according to claim 1, wherein the row signal comparing module comprises a comparator configured to:
   output a high level as a row comparison result when a voltage on the row signal output end corresponding to the row signal comparing module is no less than the threshold voltage; and
   output a low level or a zero level as a row comparison result when a voltage on the row signal output end corresponding to the row signal comparing module is less than the threshold voltage.

3. The apparatus according to claim 2, wherein the column signal comparing module comprises a comparator configured to:
   output a high level as a column comparison result when a voltage on the column signal output end corresponding to the column signal comparing module is no less than the threshold voltage; and
   output a low level or a zero level as a column comparison result when a voltage on the column signal output end corresponding to the column signal comparing module is less than the threshold voltage.

4. The apparatus according to claim 3, wherein the crystal position recognizing module is configured to:
   read a row comparison result outputted by each of the row signal comparing modules and a column comparison result outputted by each of the column signal comparing modules, and
   recognize an intersection position of a row of silicon semiconductor detectors corresponding to a row comparison result with a high level and a column of silicon semiconductor detectors corresponding to a column comparison result with a high level, as the position of the crystal hit by a photon.

5. The apparatus according to claim 1, further comprising:
   a plurality of samplers, respectively coupled to each of the row signal output ends and configured to obtain a sampled electric signal corresponding to each row of the silicon semiconductor detectors by sampling an electric signal outputted by each of the row signal output ends;
   an energy acquiring module coupled to the crystal position recognizing module and each of the samplers and configured to acquire energy of a sampled electric signal of a row including the silicon semiconductor detector corresponding to the crystal hit by a photon according to the position of the crystal hit by a photon and recognized by the crystal position recognizing module; and
   a valid event recognizing module coupled to the energy acquiring module and configured to recognize an event of hitting the crystal by a photon as a valid event when energy outputted by the energy acquiring module is within a preset energy range.

6. The apparatus according to claim 5, further comprising a plurality of amplifiers,
   wherein each of the amplifiers is respectively coupled between one of the row signal output ends and one of the samplers and configured to amplify an electric signal outputted by the one of the row signal output ends, and
   wherein each of the samplers is coupled to a respective one of the amplifiers and configured to obtain a sampled electric signal corresponding to a respective row of the silicon semiconductor detectors by sampling an electric signal amplified by the respective amplifiers.

7. The apparatus according to claim 5, further comprising n time recording modules, wherein the n is an integer no less than 2,
   wherein the silicon semiconductor detector array is divided into n groups of silicon semiconductor detectors, the n time recording modules each corresponding to a respective one of the n groups of silicon semiconductor detectors, and
   wherein each of the time recording modules is coupled to each silicon semiconductor detector in a corresponding group of silicon semiconductor detectors and the valid event recognizing module and configured to record time of occurrence of a valid event recognized by the valid event recognizing module according to a voltage outputted by each of the silicon semiconductor detectors.

8. The apparatus according to claim 5, further comprising:
   an OR logic module coupled to at least two of the row signal comparing modules and configured to carry out a logic OR operation on row comparison results outputted by the connected at least two row signal comparing modules to obtain a logic OR result; and
   a time recording module coupled to the OR logic module and the valid event recognizing module and configured to record time of occurrence of a valid event recognized by the valid event recognizing module according to a logic OR result outputted by the OR logic module.

9. The apparatus according to claim 1, further comprising:
   a plurality of samplers, respectively connected to each of the column signal output ends and configured to obtain a sampled electric signal corresponding to each column of the silicon semiconductor detectors by sampling an electric signal outputted by each of the column signal output ends;
   an energy acquiring module coupled to the crystal position recognizing module and each of the samplers and configured to acquire an energy of a sampled electric signal of a column including the silicon semiconductor detector corresponding to the crystal hit by a photon according to the position of the crystal hit by the photon and recognized by the crystal position recognizing module; and
   a valid event recognizing module coupled to the energy acquiring module and configured to recognize an event of hitting the crystal by a photon as a valid event when the energy outputted by the energy acquiring module is within a preset energy range.

10. The apparatus according to claim 9, further comprising a plurality of amplifiers,
    wherein each of the amplifiers is respectively coupled between one of the column signal output ends and one of the samplers and configured to amplify an electric signal outputted by the one of the column signal output ends, and
    wherein each of the samplers is coupled to a respective one of the amplifiers and configured to obtain a sampled electric signal corresponding to a respective column of the silicon semiconductor detectors by sampling an electric signal amplified by the respective amplifiers.

11. The apparatus according to claim 9, further comprising n time recording modules, wherein the n is an integer no less than 2,
    wherein the silicon semiconductor detector array is divided into n groups of silicon semiconductor detectors, the n time recording modules each corresponding to a respective one of the n groups of silicon semiconductor detectors, and
    wherein each of the time recording modules is coupled to each silicon semiconductor detector in a corresponding group of silicon semiconductor detectors and the valid event recognizing module and configured to record time of occurrence of a valid event recognized by the valid event recognizing module according to a voltage outputted by each of the silicon semiconductor detectors.

12. The apparatus according to claim 9, further comprising:
    an OR logic module coupled to at least two of the column signal comparing modules and configured to carry out a logic OR operation on column comparison results outputted by the connected at least two column signal comparing modules to obtain a logic OR result; and
    a time recording module coupled to the OR logic module and the valid event recognizing module and configured to record time of occurrence of a valid event recognized by the valid event recognizing module according to a logic OR result outputted by the OR logic module.

13. The apparatus according to claim 1, further comprising:
- a plurality of integrating circuits each respectively coupled to a respective one of the row signal output ends and configured to integrate an electric signal outputted by the respective one of the row signal output ends;
- a plurality of peak holding circuits coupled to a respective one of the integrating circuits and configured to hold an electric signal outputted by the respective one of the integrating circuits at a peak;
- a multiplexer coupled to the crystal position recognizing module and each of the peak holding circuits and configured to:
    - select a peak holding circuit of a row including the silicon semiconductor detector corresponding to the crystal hit by a photon from the plurality of peak holding circuits according to the position of the crystal hit by the photon in the crystal array and recognized by the crystal position recognizing module, and
    - output an electric signal of the selected peak holding circuit;
- a sampling module coupled to the multiplexer and configured to obtain a sampled electric signal by sampling an electric signal outputted by the multiplexer;
- an energy acquiring module coupled to the crystal position recognizing module and the sampling module and configured to acquire energy of a sampled electric signal outputted by the sampling module and associate the acquired energy with the position of the crystal hit by a photon and recognized by the crystal position recognizing module; and
- a valid event recognizing module coupled to the energy acquiring module and configured to recognize an event of hitting the crystal by a photon as a valid event when energy outputted by the energy acquiring module is within a preset energy range.

14. The apparatus according to claim 13, wherein the peak holding circuit comprises an amplifier and a diode, and wherein:
- one input end of the amplifier is coupled to an output end of the integrating circuit,
- an output end of the amplifier is coupled to an anode of the diode, and
- a cathode of the diode is coupled to another input end of the amplifier and the multiplexer.

15. The apparatus according to claim 13, further comprising n time recording modules, wherein the n is an integer no less than 2,
- wherein the silicon semiconductor detector array is divided into n groups of silicon semiconductor detectors, the n time recording modules each corresponding to a respective one of the n groups of silicon semiconductor detectors, and
- each of the time recording modules is coupled to each silicon semiconductor detector in a corresponding group of silicon semiconductor detectors and the valid event recognizing module and configured to record time of occurrence of a valid event recognized by the valid event recognizing module according to a voltage outputted by each of the silicon semiconductor detectors.

16. The apparatus according to claim 13, further comprising:
- an OR logic module coupled to at least two of the row signal comparing modules and configured to carry out a logic OR operation on row comparison results outputted by the connected at least two row signal comparing modules to obtain a logic OR result; and
- a time recording module coupled to the OR logic module and the valid event recognizing module and configured to record time of occurrence of a valid event recognized by the valid event recognizing module according to a logic OR result outputted by the OR logic module.

17. The apparatus according to claim 1, further comprising:
- a plurality of integrating circuits each coupled to a respective one of the column signal output ends and configured to integrate an electric signal outputted by the respective one of the column signal output ends;
- a plurality of peak holding circuits each coupled to a respective one of the integrating circuits and configured to hold an electric signal outputted by the respective one of the integrating circuits at a peak;
- a multiplexer coupled to the crystal position recognizing module and each of the peak holding circuits and configured to:
    - select a peak holding circuit of a column including the silicon semiconductor detectors corresponding to the crystal hit by a photon from the plurality of peak holding circuits according to the position of the crystal hit by the photon in the crystal array and recognized by the crystal position recognizing module, and
    - output an electric signal of the selected peak holding circuit;
- a sampling module coupled to the multiplexer and configured to obtain a sampled electric signal by sampling an electric signal outputted by the multiplexer;
- an energy acquiring module coupled to the crystal position recognizing module and the sampling module and configured to acquire energy of a sampled electric signal outputted by the sampling module and associate the acquired energy with the position of the crystal hit by a photon and recognized by the crystal position recognizing module; and
- a valid event recognizing module coupled to the energy acquiring module and configured to recognize an event of hitting the crystal by a photon as a valid event when energy outputted by the energy acquiring module is within a preset energy range.

18. The apparatus according to claim 17, wherein the peak holding circuit comprises an amplifier and a diode, and wherein:
- an input end of the amplifier is coupled to an output end of the integrating circuit,
- an output end of the amplifier is coupled to an anode of the diode, and
- a cathode of the diode is coupled to another input end of the amplifier and the multiplexer.

19. The apparatus according to claim 17, further comprising n time recording modules, wherein the n is an integer no less than 2,
- wherein the silicon semiconductor detector array is divided into n groups of silicon semiconductor detectors, the n time recording modules each corresponding to a respective one of the n groups of silicon semiconductor detectors, and
- wherein each of the time recording modules is coupled to each silicon semiconductor detector in a corresponding group of silicon semiconductor detectors and the valid event recognizing module and configured to record time of occurrence of a valid event recognized by the valid event recognizing module according to a voltage outputted by each of the silicon semiconductor detectors.

20. The apparatus according to claim 17, further comprising:
an OR logic module coupled to at least two of the column signal comparing modules and configured to carry out a logic OR operation on column comparison results outputted by the connected at least two column signal comparing modules to obtain a logic OR result; and
a time recording module coupled to the OR logic module and the valid event recognizing module and configured to record time of occurrence of a valid event recognized by the valid event recognizing module according to a logic OR result outputted by the OR logic module.

* * * * *